United States Patent
Pinza et al.

(10) Patent No.: US 7,524,886 B2
(45) Date of Patent: Apr. 28, 2009

(54) L-(−)-MOPROLOL L-(+)-TARTRATE

(75) Inventors: Mario Pinza, Corsico (IT); Caterina Maugeri, Rome (IT); Nicola Cazzolla, Albano Laziale (IT)

(73) Assignee: Aziende Chimiche Riunite Angelini Francesco A.C.R.A.F. S.p.A., Rome (IT)

(*) Notice: Subject to any disclaimer, the term of this patent is extended or adjusted under 35 U.S.C. 154(b) by 160 days.

(21) Appl. No.: 10/584,261

(22) PCT Filed: Jan. 14, 2005

(86) PCT No.: PCT/EP2005/000560

§ 371 (c)(1),
(2), (4) Date: Dec. 27, 2006

(87) PCT Pub. No.: WO2005/075408

PCT Pub. Date: Aug. 18, 2005

(65) Prior Publication Data

US 2008/0015258 A1    Jan. 17, 2008

(30) Foreign Application Priority Data

Jan. 30, 2004   (IT) .......................... MI2004A0145

(51) Int. Cl.
*A61K 31/135* (2006.01)
*C07C 211/06* (2006.01)
*C07C 215/00* (2006.01)

(52) U.S. Cl. ...................... 514/646; 564/443

(58) Field of Classification Search ................ 564/443; 514/646

See application file for complete search history.

(56) References Cited

FOREIGN PATENT DOCUMENTS

EP    0 015 418    9/1980
EP    0 118 940    9/1984

OTHER PUBLICATIONS

Berge et al. Pharmaceutical Salts. Journal of Pharmaceutical Sciences, 1977, vol. 66 (1), p. 1-19.*
Draize, John H. et al., "Methods for Study of Irritation and Toxicity of Substances Applied Topically to the Skin and Mucous Membranes", Study of Irritation and Toxicity, pp. 377-390, 1944.

* cited by examiner

*Primary Examiner*—Sikarl A Witherspoon
(74) *Attorney, Agent, or Firm*—Oblon, Spivak, McClelland, Maier & Neustadt, P.C.

(57) ABSTRACT

L-(−)-moprolol L-(+)-tartrate salt (2:1), method for preparing it and pharmaceutical composition comprising it.

9 Claims, No Drawings

L-(−)-MOPROLOL L-(+)-TARTRATE

The present invention relates to L-(−)-moprolol L-(+)-tartrate (2:1), to a method for preparing it and to a pharmaceutical composition for ophthalmic use comprising it.

IT 1 113 029 describes a process for separating the two optical isomers of moprolol.

EP-A-0 118 940 describes the use of L-(−)-moprolol or a pharmaceutically acceptable acid-addition salt thereof to produce a fluid ophthalmic composition for treating glaucoma. The pharmaceutically acceptable acid-addition salt specifically illustrated and tested in the said document is the hydrochloride.

It has now been found that the L-(+)-tartrate shows better local tolerability than the hydrochloride.

In a first aspect, the present invention thus relates to L-(−)-moprolol L-(+)-tartrate (2:1).

The salt L-(−)-moprolol L-(+)-tartrate (2:1) is readily prepared via known techniques, for instance the addition of L-(+)-tartaric acid, dissolved in a suitable organic solvent, to L-(−)-moprolol base, also dissolved in a suitable organic solvent, in a 2:1 molar ratio. The salt thus formed (L-(−)-moprolol L-(+)-tartrate (2:1)) is then isolated via known techniques including the precipitation of the salt and its filtration or via removal of the solvents by evaporation.

In one preferred embodiment, the abovementioned organic solvent is ethyl alcohol and the salt is precipitated from the acetone solution via addition of ethyl ether.

In a second aspect, the present invention thus relates to a method for preparing L-(−)-moprolol L-(+)-tartrate (2:1), characterized in that it includes the addition of L-(+)-tartaric acid, dissolved in a suitable organic solvent, to L-(−)-moprolol, also dissolved in a suitable organic solvent, in a 2:1 molar ratio.

By virtue of its better local tolerability, L-(−)-moprolol L-(+)-tartrate is found to be particularly useful for ophthalmic use.

In a third aspect, the present invention thus relates to a pharmaceutical composition for ophthalmic use, characterized in that it comprises L-(−)-moprolol L-(+)-tartrate (2:1) together with at least one pharmaceutically acceptable vehicle.

Typical examples of pathological conditions that may find benefit from treatment with a pharmaceutical composition according to the present invention are ocular hypertension and glaucoma.

Preferably, the pharmaceutical composition according to the present invention will be in the form of a gel, an ointment or eyedrops and may also include other vehicles suitable for ophthalmic use, for instance ethylene glycol, PEG, carboxymethylcellulose, mannitol, sorbitol, poloxamers, methylcellulose, hydroxyethylcellulose, hydroxypropylcellulose and the like.

The composition may also comprise other conventional ingredients such as: preserving agents, stabilizers, surfactants, buffers, salts for controlling the osmotic pressure, emulsifiers and the like.

If required for particular therapeutic uses, the pharmaceutical composition according to the present invention may comprise other pharmacologically active ingredients whose simultaneous administration is useful.

The amount of L-(−)-moprolol L-(+)-tartrate in the pharmaceutical composition of the present invention may vary within a wide range depending on known factors, for instance the particular type of disease to be treated, the seriousness of the disease and the number of daily administrations. However, a person skilled in the art may easily and routinely determine the optimum amount.

Typically, the amount of L-(−)-moprolol in the pharmaceutical composition of the present invention is between 0.01% and 20% by weight and even more preferably between 1% and 8% by weight.

The dosage forms of the pharmaceutical composition of the present invention may be prepared according to techniques that are well known to pharmaceutical chemists, including mixing, dissolution, sterilization and the like.

The examples that follow are given to illustrate the present invention without, however, limiting it.

EXAMPLE 1

Preparation of L-(−)-moprolol L-(+)-tartrate (2:1)

Step a)

2N sodium hydroxide solution was added dropwise to a solution of L-(−)-moprolol hydrochloride (10 g) in water (100 ml) with stirring, until no further precipitate was formed.

The precipitate was extracted with dichloromethane (100 ml). The organic phase was separated out and dried over sodium sulphate. Finally, the dichloromethane was removed by evaporation.

The solid residue thus obtained consisted of L-(−)-moprolol base (9.1 g).

Step b)

A solution of L-(+)-tartaric acid (1.57 g; 0.01 mol) in absolute ethanol (15 ml) was added to a solution of L-(−)-moprolol base (5.0 g; 0.02 mol) in hot absolute ethanol (30 ml).

After stirring the solution at 60° C. for 10 minutes, ethyl ether was added until precipitation was complete. The precipitate thus obtained (very hygroscopic) was separated out by decantation and crystallized from absolute ethanol (30 ml) to give the desired product (5.2 g).

m.p.=135° C. $[\alpha]=-1.1$ (c=5 in $H_2O$)

Elemental Analysis

| Elemental Analysis For $C_{30}H_{48}N_2O_{12}$ | C | H | N |
|---|---|---|---|
| Calculated | 57.31 | 7.70 | 4.46 |
| Found | 57.16 | 7.79 | 4.38 |

Test 1

Ocular Tolerability

Two aqueous solutions were used.

The first contained 1% by weight of L-(−)-moprolol hydrochloride (corresponding to 0.87% by weight of L-(−)-moprolol). The second contained 1.14% by weight of L-(−)-moprolol L-(+)-tartrate (2:1) (corresponding to 0.87% by weight of L-(−)-moprolol).

12 male rabbits (New Zealand White) with an average weight of 2 kg and an average age of ten months were used, divided into two groups of six rabbits each. The first group was treated with 0.1 ml of the first test solution three times a day for fifteen days. The second group was treated with 0.1 ml of the second test solution three times a day for fifteen days.

The tolerability was evaluated according to J. Draize et al., Pharmacol. Exp. Ther., 83, 377-390 (1944). The results are shown in Table 1 below.

TABLE 1

|  |  | Before the first application L-(−)-moprolol hydrochloride | After the last application L-(−)-moprolol L-(+)-tartrate |
|---|---|---|---|
| Conjunctiva | Reddening | 1 | 0 |
|  | Swelling | 2 | 0 |
|  | Lachrymation | 2 | 1 |
| Iris |  | 0 | 0 |
| Cornea | Opacity | 0 | 0 |
|  | Area of the cornea affected by opacity | 0 | 0 |
|  | Total Score | 5 | 1 |

The invention claimed is:

1. L-(−)-moprolol L-(+)-tartrate salt (2:1).

2. Pharmaceutical composition for ophthalmic use, characterized in that it comprises L-(−)-moprolol L-(+)-tartrate (2:1) together with at least one pharmaceutically acceptable vehicle.

3. Pharmaceutical composition according to claim 2, characterized in that it is in the form of a gel, an ointment or eyedrops.

4. Pharmaceutical composition according to claim 2 or 3, characterized in that the amount of L-(−)-moprolol is between 0.01% and 20% by weight.

5. Pharmaceutical composition according to claim 2 or 3, characterized in that the amount of L-(−)-moprolol is between 1% and 8% by weight.

6. Process for preparing L-(−)-moprolol L-(+)-tartrate (2:1), characterized in that it includes the addition of L-(+)-tartaric acid, dissolved in a suitable organic solvent, to L-(−)-moprolol base, also dissolved in a suitable organic solvent, in a 2:1 molar ratio.

7. Process according to claim 6, characterized in that the salt thus formed is isolated via precipitation and filtration.

8. Process according to claim 6 or 7, characterized in that the abovementioned organic solvent is ethyl alcohol.

9. Process according to claim 8, characterized in that the salt is precipitated from the ethanolic solution via addition of ethyl ether.

* * * * *